United States Patent [19]
Kligman

[11] Patent Number: 5,998,395
[45] Date of Patent: Dec. 7, 1999

[54] METHODS OF TREATING INFLAMMATORY DERMATOSIS

[76] Inventor: Albert M. Kligman, Philadelphia, Pa.

[21] Appl. No.: 08/119,510

[22] Filed: Sep. 10, 1993

Related U.S. Application Data

[63] Continuation of application No. 07/832,828, Feb. 7, 1992, abandoned.

[51] Int. Cl.[6] ............................ A61K 31/56; A61K 31/20
[52] U.S. Cl. ......................... 514/171; 514/180; 514/559; 514/555
[58] Field of Search .................................... 514/171, 180, 514/559, 555

[56] References Cited

U.S. PATENT DOCUMENTS

| | | | |
|---|---|---|---|
| 3,729,568 | 4/1973 | Kligman | 424/318 |
| 4,126,693 | 11/1978 | Gander et al. | 424/282 |
| 4,487,782 | 12/1984 | Mezick | 424/317 |
| 4,889,847 | 12/1989 | Kligman et al. | 514/171 |
| 5,019,569 | 5/1991 | Kligman e tal. | 514/171 |

FOREIGN PATENT DOCUMENTS 7700678   8/1978   South Africa.

OTHER PUBLICATIONS

Stoughton, R.B., "Percutaneous Absorption of Drugs," *Annual Review of Pharmacologic Toxicology*, pp. 55–69 (1989).

Giannotti, B. and Stuttgen, G. (Editors), *Drugs* (Supplement 5), vol. 36, pp. 1–61 (1988).

Albert M. Kligman, "Adverse Effects of Topical Corticosteroids," *Topical Corticosteroid Therapy: A Novel Approach to Safer Drugs*, pp. 181–187 (1988).

Kays H. Kaidbey, M.D. et al., "Treatment of Psoriasis with Topically Applied Tretinoin and Steriod Ointment," *Arch Dermatol 111*, pp. 1001–1003 (1975);.

P. Frost et al., "Retinoic Acid for the Therapy of Psoriasis," *Acta Derma–tovener* (Stockholm), Suppl. 74, pp. 155–160 (1975);.

J.R. Thomas,III, M.D. et al., "The Therapeutic Uses of Topical Vitamin A Acid," *Journal of the American Academy of Dermatology 4*, No. 6, pp. 505–516 (1981);.

*Primary Examiner*—Theodore J. Criares
*Attorney, Agent, or Firm*—Panitch Schwarze Jacobs & Nadel, P.C.

[57] ABSTRACT

Inflammatory dermatoses are controlled and cleared by topical application to the affected areas of the skin of a composition containing both a corticosteroid and a retinoid. The combined therapy is more effective than either active ingredient alone and is particularly effective for chronic dermatoses which are or have become resistant to corticosteroid treatment alone. After clearing has been obtained with once or twice daily applications of the corticosteroid-retinoid composition, usually after several weeks, clearance can be maintained by less frequent application or lower concentrations of the composition or by application of only one of the corticosteroid or retinoid, less potent corticosteroids, or other non-steroidal therapies, depending upon the particular dermatosis being treated.

6 Claims, No Drawings

METHODS OF TREATING INFLAMMATORY DERMATOSIS

CROSS-REFERENCE TO RELATED APPLICATION

This application is a continuation of co-pending application Ser. No. 07/832,828, filed Feb. 7, 1992, now abandonded.

FIELD OF THE INVENTION

The present invention relates to methods for the treatment of inflammatory dermatoses. More particularly, the invention is directed to controlling, clearing and maintaining the clearance of inflammatory dermatoses by administering topical compositions to the affected areas of the skin.

BACKGROUND OF THE INVENTION

The most widely prescribed drugs to treat dermatologic disease are corticosteroids, also known as glucocorticosteroids or glucocorticoids. Approximately 50% of prescriptions written by dermatologists are for topical corticosteroids. Since the introduction of these substances in the early 1950s for dermatologic diseases, topical corticosteroid therapy continues to be the mainstay for the management of a broad spectrum of inflammatory dermatoses. Although systemic corticosteroids are often required in some severe dermatologic diseases, topical treatment is preferred in most responsive cases because it causes fewer systemic adverse effects.

Topical corticosteroids are generally effective in the treatment of acute and chronic dermatoses such as seborrheic dermatitis, atopic dermatitis, contact dermatitis of the irritant and allergic type, localized neurodermatitis (lichen simplex chronicus), lichen planus, and psoriasis. Steroids are also used for a variety of other less common conditions, such as Darier's disease and ichthyosiform dermatitis. A good overview of topical corticosteroid therapy appears in a series of papers presented at the Symposium on Topical Corticosteroids Today and Tomorrow, sponsored by Schering AG in Bali, Jun. 16–20, 1988, which were published in *Drugs* 36, Supplement 5, pp. 1–61 (Adis Press Ltd. 1988).

Individual topical corticosteroid preparations vary in anti-inflammatory potency and clinical efficacy. Therapeutic efficacy of steroid therapy can often be enhanced by increasing the potency of the steroid or by using special enhancers, such as occlusive dressings. In general, efficacy is dependent on multiple factors, viz. vehicle, site and frequency of application, disease, the individual patient, use of occlusive dressings, etc.

Potency of the corticosteroid preparation varies according to the particular corticosteroid selected, its concentration, and its vehicle. For convenience, topical corticosteroids, are classified into seven groups from most (Group I) to least (Group VII) potent as shown, for example, in Table I below. Further, these classifications are ranked according to relative potency designations with Group I usually designated as ultra high potency, Groups II and II designated as high potency, Groups IV and V designated mid potency, and Groups VI and VII designated low potency. Representative commercial corticosteroid preparations are set forth and classified according to this system in R. B. Stoughton, "Percutaneous Absorption of Drugs," *Annual Review of Pharmacologic Toxicology*, pp. 55–69 (1989).

TABLE I

POTENCY RANKING OF TOPICAL CORTICOSTEROIDS
(Group I, most potent to Group VII, least potent)

| Group Potency | Generic Name | Dosage Form | Usual Concentration |
|---|---|---|---|
| I. | Betamethasone dipropionate | cream, ointment | 0.05% |
| | Clobetasol propionate | cream, ointment | 0.05% |
| | Diflorasone diacetate | ointment | 0.05% |
| II. | Amcinonide | cream, ointment | 0.1% |
| | Betamethasone dipropionate | ointment | 0.05% |
| | Diflorasone diacetate | ointment | 0.05% |
| | Halcinonide | cream, ointment | 0.1% |
| | Fluocinonide | cream, ointment, solution, gel | 0.05% |
| | Desoximetasone | cream, gel, ointment | 0.05%–0.25% |
| | Triamcinolone acetonide | cream, ointment | 0.5% |
| | Mometasone | ointment | 0.1% |
| | Fluocinolene acetonide | cream | 0.2% |
| III. | Triamcinolone acetonide | ointment | 0.1% |
| | Betamethasone dipropionate | cream | 0.05% |
| | Diflorasone diacetate | cream | 0.05% |
| | Betamethasone valerate | ointment | 0.1% |
| | Mometasone | cream | 0.1% |
| IV. | Flurandrenolide | ointment | 0.05% |
| | Triamcinolone acetonide | cream, lotion | 0.1% |
| | Fluocinolone acetonide | ointment | 0.025% |
| | Desoximetasone | cream | 0.05% |
| | Clocortolone pivalate | cream | 0.1% |
| V. | Flurandrenolide | cream | 0.05% |
| | Betamethasone dipropionate | | 0.05% |
| | Triamcinolone acetonide | lotion | 0.1% |
| | Hydrocortisone butyrate | cream, ointment | 0.1% |
| | Fluocinolone acetonide | cream | 0.025% |
| | Betamethasone valerate | cream | 0.1% |
| | Hydrocortisone valerate | cream | 0.2% |

TABLE I-continued

POTENCY RANKING OF TOPICAL CORTICOSTEROIDS
(Group I, most potent to Group VII, least potent)

| Group Potency | Generic Name | Dosage Form | Usual Concentration |
|---|---|---|---|
| VI. | Desonide | cream, ointment | 0.05% |
| | *Fluocinolone acetonide* | solution | 0.01 |
| | *Betamethasone valerate* | lotion | 0.05% |
| | *Aciometasone dipropionate* | cream, ointment | 0.05% |
| VII. | Topicals with hydrocortisone, dexamethasone, flumethalone, prenisolone, and methyprednisolone | | |

Though some steroids, particularly mid- to high-potency steroids, are efficacious in chronic dermatoses, long term use of steroids is associated with serious local side effects. These include skin atrophy (thinning, telangiectasia, striae) and a prompt rebound flare when the steroid is stopped. Treatment of large areas of skin and use of occlusive dressings can also increase the potential for adverse effects. This is especially the case in children. As discussed more fully below, U.S. Pat. Nos. 4,889,847 and 5,019,569 disclose the use of retinoids, such as tretinoin, to prevent and reverse skin atrophy induced by corticosteroid therapy.

Topical retinoids such as tretinoin (all-trans-retinoic acid or Vitamin A acid) have been used by dermatologists for almost twenty years. For example, tretinoin is used topically in the treatment of acne vulgaris, primarily grades I–III, in which comedones, papules, and pustules predominate. See, for example, U.S. Pat. No. 3,729,568 of Kligman.

Tretinoin has been used effectively in the treatment of other skin conditions such a psoriasis, congenital ichthyosiform erythroderma, Darier's disease, epidermolytic hyperkeratosis, actinic keratosis, trichostasis, flat warts, basal cell carcinomas, and a variety of unrelated disorders. See, for example, J. R. Thomas et al. "The Therapeutic Uses of Topical Vitamin A Acid," *Journal of the American Academy of Dermatology*, 4:505–513 (1981).

More recently, it has been found that retinoids, such as tretinoin, particularly when used in separate, sequential topical applications with the corticosteroid, prevent and reverse skin atrophy in patients on long term corticosteroids for various skin diseases. See, for example, U.S. Pat. Nos. 4,889,847 and 5,019,569 of Kligman, Mezick and Capetola, the disclosures of which are incorporated herein by reference. However, that work was concerned with preventing and reversing the side effects of corticosteroid therapy and did not address the possibility of enhanced efficacy, especially for those patients whose disease has become resistant to corticosteroids. Dermatologists call this acquired resistance "tachyphylaxis" and try to mitigate it by various strategies, such as rest periods (interval therapy) and switching to another drug. These approaches are only marginally helpful.

BRIEF SUMMARY OF THE INVENTION

According to the present invention inflammatory dermatoses, including both chronic and acute varieties, can be controlled and cleared more effectively than with the use of corticosteroids or retinoids alone by topically administering to the affected areas of the skin a composition comprising a corticosteroid and a retinoid in amounts which are effective for treating the dermatoses. That is, these two drugs have entirely different modes of action and, when combined in a single formulation, have synergistic effects which lead to more rapid clearing and are notably effective in dermatoses which have not responded to either corticosteroids or retinoids alone. Typically, the dermatoses can be controlled and cleared by once or twice daily applications of a composition containing both the retinoid and the corticosteroid in a pharmaceutically acceptable carrier for about two to three weeks.

Thereafter, clearance can be maintained by less frequent and/or less potent applications of one or both of the active ingredients, such as a corticosteroid several times per week or a daily application of a retinoid. Moreover, once the disease has been brought under control, lower potency steroids can be used to maintain the remission or other non-steroidal regimens can be used which are safer, though usually less effective, viz. tars, topical antibiotics or antibacterials, and other conventional therapies. The physician is given more choices in handling inflammatory dermatoses, particularly chronic inflammatory dermatoses, which are merely controlled but not cured by corticosteroids.

DETAILED DESCRIPTION OF THE PREFERRED EMBODIMENTS

The inflammatory dermatoses which may be treated according to the present invention are well known in the art. They include chronic and stubborn, as well as acute, afflictions of the skin which have previously been treated with various anti-inflammatory drugs, including oral corticosteroids and sometimes oral retinoids. While these prior therapies are sometimes effective, the side effects of each are numerous and severe.

There have been reports of using tretinoin and certain corticosteroids in combination, either sequentially or mixed together, for various forms of psoriasis. See, for example, K. H. Kaidbey et al., "Treatment of Psoriasis with Topically Applied Tretinoin and Steroid Ointment," *Archives of Dermatology*, 111:1001–1003 (1975) and P. Frost et al., "Retinoic Acid for the Therapy of Psoriasis", *Acta Dermatovener*, Suppl. 74:154– 160 (Stockholm, 1975). However, effective treatment of inflammatory dermatoses in general has not previously been indicated.

Among the disorders which can be effectively treated according to the present invention are the various forms of inflammatory acne. These include the most devastating type, acne conglobata or nodulocystic acne. Additionally, inflammatory acne with numerous pustules and deep persistent papules responds dramatically.

Severely inflammatory acne, notably acne conglobata, responds to an oral retinoid, 13-cis retinoic acid (available commercially as ACCUTANE®). However, the side effects of this drug are very serious, including teratogenicity, elevated blood lipids, fragile skin, conjunctivitis, etc. It has been found that acne conglobata as well as severely inflammatory acne vulgaris, in particular, can be brought under control or show excellent responses in as little as two to three weeks of twice daily applications of the combination treatment of the present invention. Persistent papulopustular acne also responds well to the combination treatment of the invention. It is noted that acne vulgaris is actually a mixture of inflammatory and non-inflammatory acnes, and while the treatments according to the present invention could be used for non-inflammatory acne as well, such use would probably be unnecessary in most cases due to the effectiveness of retinoids alone.

Rosacea is another common disease which can be very inflammatory and is resistant to therapy except for oral retinoids. Severe rosacea mimics acne conglobata. These fulminating types of rosacea also respond to the combination of a retinoid and a corticosteroid according to the present invention.

Other inflammatory disorders which may be controlled and cleared by the treatments of the present invention include lichen planus, especially the hypertrophic variety; chronic discoid lupus erythematosus; chronic atopic dermatitis, including lichen simplex chronicus which is a persistent, itchy dermatosis that is common in patients with atopic dermatitis; chronic contact or allergic dermatitis, which is due to a great variety of environmental allergens; chronic hand dermatitis; lichen amyloidosis; alopecia areata; pseudofolliculitis barbae; pityriasis rubra pilaris; mycosis fungoides; drug reactions (acute); and others.

The corticosteroids useful in the treatments according to the present invention include all of the large number of corticosteroids which are known for their anti-inflammatory properties. See, for example, those listed in Table I above. Preferably, the mid- to high- or ultra high-potency corticosteroids are used in the invention. Examples of preferred mid-potency corticosteroids are betamethasone valerate, triamcinolone acetonide, and fluocinolone acetonide. Clobetasol propionate is presently unrivalled in potency. Other preferred high-potency steroids include, for example, betamethasone dipropionate. It is also possible to use low-potency corticosteroids such as hydrocortisone, dexamethasone and prednisolone in those particular chronic dermatoses, such as atopic dermatitis, which do not require high-potency steroids for control.

Retinoids have been defined narrowly as comprising vitamin A (retinol) and its derivatives, such as vitamin A aldehyde (retinal) and vitamin A acid (retinoic acid), which are metabolites of natural vitamin A. However, subsequent research has resulted in a larger class of chemical compounds that are termed retinoids because they have biological actions similar to the parent vitamin A, even though there may be great structural dissimilarities. Compounds useful in the present invention include all natural and/or synthetic analogs of vitamin A or retinol-like compounds which have similar therapeutic activities as demonstrated for a variety of retinoids. Accordingly, as used herein for purposes of the present invention, the term "retinoid" will be understood to mean a natural or synthetic substance that elicits all or some of the biologic responses of retinoic acid or retinol by binding to and subsequently activating known and unknown cutaneous retinoic acid receptors. Examples of suitable retinoids useful in the present invention are set forth in Table I, although it will be understood that the invention is not limited thereto.

TABLE I all-trans-retinoic acid
13-cis-retinoic acid
11-cis-retinoic acid
9-cis-retinoic acid
retinol
retinal
retinoyl palmitate
retinyl palmitate
retinyl propionate
(all-E)-9-(4-methoxy-2,3,6-trimethylphenyl)-3,7-dimethyl-2,4,6,8-nonatetraenoic acid ethyl ester
(all-E)-9-(4-methoxy-2,3,6-trimethylphenyl)-3,7-dimethyl-2,4,6,8-nonatetraenoic acid
N-ethyl-9-(4-methoxy-2,3,6-trimethyl-nonatetraenamide
(E,E)-9-(2,6-dichloro-4-methoxy-3-methylphenyl)-3,7-dimethyl-2,4,6,8-nonatetraenoic acid ethyl ester
7,8-didehydroretinoic acid
(E,E)-4-[2-methyl-4-(2,6,6-trimethyl-1-cyclohexen-1-yl)-1,3-butadienyl]benzoic acid
(E)-4-[4-methyl-6-(2,6,6-trimethyl-1-cyclohexen-1-yl)-1,3,5-hexa-trienyl]benzoic acid
(all-E)-3,7-dimethyl-(3-thienyl)-2,4,6,8-nonatetraenoic acid
(E,E,E)-3-methyl-7-(5,6,7,8-tetrahydro-5,5,8,8y-tetramethyl-2-naphthalenyl)-2,4,6-octatrienoic acid
(E)-6-[2-(2,6,6-trimethyl-1-cyclohexen-1-yl)ethynyl]-2-naphthalenecarboxylic acid
(E,E,E)-7-(2,3-dihydro-1,1,3,3-tetra-methyl-1H-inden-5-yl)-3-methyl-2,4,6-octatrienoic acid
(E)-4-[2-(2,3,-dihydro-1,1,3,3,-tetramethyl-1H-inden-5-yl)-1-propenyl[benzoic acid
(E)-4-[2-(5,6,7,8-tetrahydro-5,5,8,8-tetramethyl-2-naphthalenyl-1-propenyl]benzoic acid
(E)-4-[2-(5,6,7,8-tetrahydro-3-methyl-5,5,8,8-tetramethyl-2-naphthalenyl-1-propenyl[benzoic acid
(E)-1,2,3,4-tetrahydro-1,1,4,4-tetramethyl-6-(1-methyl-2-phenylethenyl)naphthalene
6-(1,2,3,4-tetrahydro-1,1,4,4-tetramethyl-6-naphthyl-2-naphthalenecarboxylic acid
(E)-6-[2-(4-ethylsulfonyl)phenyl]-1-methytethenyl]-1,2,3,4-tetrahydro-1,1,4,4-tetramethylnaphthalene
4-[(5,6,7,8-tetrahydro-5,5,8,8-tetramethyl-2-naphthalenyl)ethynyl]benzoic acid
(E)-2-(1,1,4,4-tetramethyl-1,2,3,4-tetra-hydronaphth-7-yl)-1-[4-tetrazol-5-yl)phenyl]-1-propene
(E)-4-[2-(5,6,7,8-tetrahydro-7-hydroxy-5,5,8,8-tetramethyl-2-naphthalenyl)-1-propenyl]benzyl alcohol
(6-(3-(1-adamantyl)-4-methoxyphenyl)-2-naphthoic acid)
11-cis,13-cis-12-hydroxymethylretinoic acid δ-lactone
4-acetamidophenyl retinoate
1-(4-carboxyphenyl)-4-(5,6,7,8-tetrahydro-5,5,8,8-tetramethyl-2-naphthalenyl)pyrazole
1(4-carboxyphenyl)-5-hydroxy-3-(5,6,7,8-tetrahydro-5,5,8,8-tetramethyl-2-naphthalenyl)pyrazole
4-[(5,6,7,8-tetrahydro-5,5,8,8-tetramethyl-2-naphthalenyl)-ethynyl]methylsulfonylbenzene
retinoyl β-glucuronide
4-[(5,6,7,8-tetrahydro-5,5,8,8-tetramethyl-2-naphthalenyl)carbamoyl]benzoic acid
4-[(5,6,7,8-tetrahydro-5,5,8,8-tetramethyl-2-naphthalenyl)carboxamido]benzoic acid Also encompassed within the term "retinoid" are geometric and stereoisomers of the retinoids, as well as pro-drugs thereof.

Preferably, the corticosteroid and retinoid are applied simultaneously in a single composition which uses a carrier pharmaceutically acceptable for both the retinoid and corticosteroid. Since tretinoin and some other actives are relatively unstable, such as being subject to photodecomposition, the particular combination of corticosteroid, retinoid, vehicle and any other ingredients must be selected so as to be compatible, but such selection is within the skill of the art given the present disclosure. The amounts or concentrations of the corticosteroid and retinoid which are present in the composition will vary widely depending upon such factors as the particular corticosteroid and retinoid chosen, the disorder being treated, the frequency of applications to be made, whether or not the administration will include he use of an occlusive dressing, etc.

Pharmaceutical compositions containing a retinoid as an active ingredient in intimate admixture with a pharmaceutical carrier are known in the art and can be prepared according to conventional pharmaceutical compounding techniques, such as those used for formulating topical all-trans-retinoic acid (tretinoin). The carrier may take a wide variety of physical forms such as creams, dressings, gels, lotions, ointments or liquids. The particular retinoid, which may be more or less potent than tretinoin, will be present in an amount from about 0.00001% by weight to about 3% by weight, depending on the potency of the retinoid. Suitable topical retinoid preparations which are commercially available are Retin-A® gels which contain 0.01% to 0.025% by weight tretinoin, and Retin-A® creams, which contain 0.025% to 0.1% by weight tretinoin, both produced by Ortho Pharmaceutical Corporation.

Typically, the corticosteroid will be present in the composition in amounts of about 0.00001 to 3 weight percent, mainly depending on desired potency. Using tretinoin as the standard for retinoids, tretinoin will typically be present in the composition in an amount of about 0.0001 to 1 weight percent, and other more or less potent retinoids will be used in corresponding amounts equivalent thereto.

Low potency corticosteroids, such as hydrocortisone, will generally require concentrations of about 2% or higher, whereas mid- to high-potency corticosteroids are generally satisfactory at the concentrations recommended by their manufacturers, such as 0.1% for betamethasone valerate or triamcinolone acetonide, and 0.05% for clobetasol propionate. These concentrations can of course be altered to obtain an optimal formulation for a particular condition. Moreover, a particular advantage of the combinations of the present invention is that the corticosteroid can often be used in concentrations half of those in present formulations (not containing a retinoid). This is an added safety factor.

Thus, on the one hand for relatively easily treated conditions, the enhanced efficacy provided by the combination with the retinoid allows the use of lower concentrations of the corticosteroid. On the other hand, for particularly resistant disorders which would not normally be controlled or cleared by either the corticosteroid or retinoid alone, higher concentrations of the corticosteroid may be desired and may be more easily tolerated due to the presence of the retinoid.

The compositions of the invention may also contain additional ingredients known in the art, such as stabilizers, emollients, penetration enhancers, and the like. Also, the compositions may be used with various means of application including, for example, occlusive dressings and drug delivery systems such as sponges, patches, liposomes, etc.

The general therapeutic regimen or strategy using the combination of the present invention usually involves once or twice daily applications, preferably twice daily, of the combination for several weeks to bring the dermatoses under control. Thereafter, depending on the characteristics of the disease it is possible to maintain clearance by judicious application of the corticosteroid alone several times weekly or by daily application of the retinoid alone, or by lower concentrations, and/or less frequent applications of the combination or of a less potent combination.

Atopic dermatitis is an example of a disorder in which the clearance can be maintained by application of a low-potency corticosteroid alone, while inflammatory acne vulgaris is an example of a disorder in which clearance can be maintained by application of a retinoid, e.g. tretinoin, alone.

Controlled studies on a significant number of patients have shown that the combined therapy according to the present invention is not only additive, but may be truly synergistic. That is, the combination is more effective than and produces responses not obtained by the usual treatment regimens with either the corticosteroid or the retinoid alone. Thus, inflammatory dermatoses clear more rapidly and there is rapid resolution of scaling, induration and edema with the combination. This leads to greater patient compliance. Moreover, relapses are delayed and less severe. Significantly, improvement has been demonstrated in conditions which have become refractory to standard or conventional treatments, such as corticosteroid therapy alone, and rebound, often found after stopping steroid therapy, is eliminated.

It is important to note that the function of the retinoid component in this combination therapy is not simply that of preventing or reversing atrophogenicity of the corticosteroid, as described and claimed in U.S. Pat. Nos. 4,889,847 and 5,019,569. According to the discovery of the present invention, the retinoid enhances the efficacy of the corticosteroid in suppressing inflammation which is characteristic of these chronic and acute dermatoses. It is known that tretinoin and other retinoids have some anti-inflammatory effects, though the mechanism of action is very different from that of corticosteroids. It is also known that tretinoin makes the skin more permeable, enabling a greater amount of steroid to reach the diseased skin.

While applicant does not wish to be bound by any particular theory of action, it is believed that the retinoid enhances the efficacy of the corticosteroid in at least two particular ways: (1) by thinning the outer horny layer (the so-called permeability "barrier" of the skin), thus enabling more of the drug to penetrate into the target tissue and yielding a greater local concentration of the corticosteroid (equivalent to increasing the dose of the corticosteroid); and (2) the capacity of the retinoid to prevent and reduce inflammation in its own right.

The possible explanations for the anti-inflammatory effects relate to the known ability of retinoids to inhibit migration of white cells (neutrophils) from the blood vessels into the tissue (chemotaxis). Moreover, retinoids influence immune processes; for example, activation of T-cells and the release of cytokines at the site of inflammation. Retinoids also inhibit migration of macrophages into diseased areas. These cells produce a variety of toxic products, including interleukins and proteins. One can cite other anti-inflammatory effects for which there is as yet no obvious explanation. Tretinoin brings about faster resolution of chronic granulomas that are the result of foreign body reactions such as those elicited after the injection of collagen, elastin and carrageenin.

It must be emphasized that the modes of action of corticosteroids and retinoids are completely different, and hence the combination of the two has unexpected beneficial therapeutic effects. One mechanism by which the corticosteroid works is by inhibiting the release of enzymes that initiate the inflammatory cascade, whereas the effect of the retinoid is less specific and dependent on a multiplicity of unrelated effects. Among these is the ability of retinoids to promote wound healing and to stimulate the formation of new blood vessels (angiogenesis), thus increasing the local blood supply. Overall, retinoids, while initially inflammatory, seem to moderate inflammatory processes. In sum, the corticosteroid-retinoid combinations of the invention blunt inflammation by two entirely different mechanisms, acting in concert.

Another advantage of the combination is the prevention of rebound flare when the steroid is withdrawn. Dramatic examples of rebound flare are well known to dermatologists. For example, the treatment of rosacea by topical steroids leads to a syndrome called "steroid rosacea" in which atrophy and redness are prominent. After cessation of treatment, a ferocious, intense, pustular eruption develops which is very difficult to control. In other diseases too, the treated sites show a "rebound dermatitis" when the steroid is stopped. The site becomes tender, red, cracked, edematous and peeling. This rebound is completely prevented with combinations according to the present invention. Still further, tachyphylaxis has not been observed with the combinations according to the present invention.

The present invention will now be described in more detail with reference to the following specific, non-limiting examples. In these examples, two formulations have been extensively evaluated: (1) 0.1% triamcinolone acetonide combined with 0.1% tretinoin in a cream base; and (2) 0.05% clobetasol propionate combined with 0.1% tretinoin in a cream base. As expected, the therapeutic response to the latter formulation was swifter, because clobetasol is the most potent corticosteroid known. Unless otherwise indicated in the following examples, the combination brought about rapid resolution (control and clearing) within two to three weeks of twice daily applications.

EXAMPLE 1

Approximately 30 cases of highly inflammatory acne vulgaris were treated with a combination of 0.05% clobetasol propionate and 0.1% tretinoin in a cream base. Almost every instance of this condition was brought under control within two to three weeks of twice daily applications.

EXAMPLE 2

About 20 patients having severely inflammatory acne conglobata were treated with the same combination as in Example 1. These patients have shown excellent responses in three weeks of twice daily applications. The response (clearing) is faster and more dramatic than with oral 13-cis-retinoic acid.

EXAMPLE 3

Nine cases of severe papulo-pustular inflammatory acne were treated for two to three weeks with twice daily applications of 0.1% triamcinolone acetonide and either 0.05 or 0.1% tretinoin in a water-in-oil cream. The lesions cooled down quickly and were then switched to daily applications of 0.025% tretinoin cream alone. Another alternative after stopping the combination treatment is a topical antibiotic such as erythromycin or an anti-bacterial such as benzoyl peroxide.

EXAMPLE 4

Approximately 14 patients with severely inflamed rosacea of the face have been treated with a combination of 0.1% tretinoin and 0.05% clobetasol propionate in a cream base. This combination was remarkably effective in clearing granulomatous rosacea, pyoderma faciale, and rosacea fulminans. Thereafter, remission could be maintained by topical metronidazole or oral tetracycline.

EXAMPLE 5

Six patients with hypertrophic lichen planus of the legs responded rapidly (within three weeks) from twice daily applications of the same combination as in Example 4. Clearing could be maintained by mid-strength corticosteroids applied every second to third day.

EXAMPLE 6

Ten adults with the adult form of chronic atopic dermatitis, which appeared as lichen simplex chronicus of he lower legs were treated with a combination of 0.025% or 0.05% tretinoin and 2.0% hydrocortisone in a cream vehicle. The itchy, thick plaques which characterize this condition essentially disappeared within three weeks of twice daily applications of the combination. Thereafter, 1.0% hydrocortisone cream, applied once daily, was sufficient to prevent relapse.

EXAMPLE 7

A dozen patients suffering from chronic allergic contact dermatitis of occupational origin responded quickly to treatment with applications of the combination of 0.1% triamcinolone acetonide and 0.1% tretinoin in a cream base.

EXAMPLE 8

Twenty black males with long-standing, severely inflammatory pseudofolliculitis barbae were treated with the combination of 0.1% triamcinolone acetonide and 0.1% or 0.05% tretinoin in a petrolatum vehicle (water-in-oil emulsion containing 46% petrolatum). In this disease tips of highly curved, stiff beard hairs which grow downwards into the skin create an inflammatory foreign body granuloma. After about two to three weeks of treatment with the combination, the inflammatory lesions flattened and became inactive, after which tretinoin alone was used for maintenance.

EXAMPLE 9

Small numbers of patients with various chronic dermatoses characterized by chronic, resistant, inflammatory lesions responded favorably to daily applications of the combination of 0.05% clobetasol propionate and 0.1% tretinoin in a cream base for three to four weeks. These disorders included chronic discoid lupus erythematosus, lichen planus, Darier's disease, alopecia areata, and persistent seborrheic dermatitis.

The present invention may be embodied in other specific forms without departing from the spirit or essential attributes thereof and, accordingly, reference should be made to the appended claims, rather than to the foregoing specification as indicating the scope of the invention.

I claim:

1. A method of suppressing inflammation in inflammatory dermatoses to effect controlling and clearing of an inflammatory dermatosis selected from the group consisting of inflammatory acne vulgaris, inflammatory acne conglobata, inflamed rosacea, granulomatous rosacea, pyoderma faciale, rosacea fulminans, hypertrophic lichen planus, chronic discoid lupus erythematosus, lichen planus, Darier's disease, alopecia areata, and persistent seborrheic dermatitis, comprising topically administering to an area of skin affected by the dermatosis a composition comprising clobetasol propionate and tretinoin, said clobetosal propionate and tretinoin being present in synergistic effective amounts which are effective to suppress said inflammation and control and clear said dermatosis.

2. The method according to claim 1, wherein the composition comprises 0.05 wt % clobetasol propionate and 0.1 wt % tretinoin.

3. A method of suppressing inflammation in inflammatory dermatoses to effect controlling and clearing of an inflammatory dermatosis selected from the group consisting of papulo-pustular inflammatory acne, chronic allergic contact dermatitis and inflammatory pseudofolliculitis barbae, comprising topically administering to an area of skin affected by the dermatosis a composition comprising triamcinolone acetonide and tretinoin, said triamcinolone acetonide and tretinoin being present in synergistic effective amounts which are effective to suppress said inflammation and control and clear said dermatosis.

4. The method according to claim 3, wherein the composition comprises 0.1 wt % triamcinolone acetonide and 0.05 to 0.1 wt % tretinoin.

5. A method of suppressing inflammation in chronic atopic dermatitis to effect controlling and clearing of said dermatitis, comprising topically administering to an area of skin affected by the dermatitis a composition comprising hydrocortisone and tretinoin, said hydrocortisone and tretinoin being present in synergistic effective amounts which are effective to suppress said inflammation and control and clear the dermatitis.

6. The method according to claim 5, wherein the composition comprises 2.0 wt % hydrocortisone and 0.025 to 0.05 wt % tretinoin.

* * * * *